United States Patent [19]
Reuland

[11] 4,024,394
[45] May 17, 1977

[54] METHOD AND APPARATUS FOR MEASURING AND REGULATING THE DENSITY OF ROD-LIKE FILLERS CONSISTING OF TOBACCO OR THE LIKE

[75] Inventor: Joachim Reuland, Hamburg, Germany

[73] Assignee: Hauni-Werke Körber & Co., KG, Hamburg, Germany

[22] Filed: Sept. 12, 1975

[21] Appl. No.: 613,030

Related U.S. Application Data

[63] Continuation of Ser. No. 480,871, June 19, 1974, abandoned.

[30] Foreign Application Priority Data

June 22, 1973  Germany ..................... 2331855

[52] U.S. Cl. ......................... 250/308; 250/359
[51] Int. Cl.² ................................... G01N 23/00
[58] Field of Search ..................... 250/308, 359

[56] References Cited

UNITED STATES PATENTS 2,832,352   4/1958   Powell ............................. 250/308
3,648,035   3/1972   Hart ................................ 250/359

Primary Examiner—Harold A. Dixon

Attorney, Agent, or Firm—Peter K. Kontler; John Kurucz

[57] ABSTRACT

The density of a rod-like tobacco filler in a cigarette making machine is measured and regulated by placing a source of beta radiation adjacent to one side of the moving filler and a transducer at the other side of the filler opposite the source whereby the transducer furnishes a continuous series of electric signals which indicate the weakening of beta rays during passage through successive minute increments of the filler as a function of density of the corresponding increments as well as fluctuations in the intensity of beta rays due to stochastic disintegration of nuclei in the source. The signals from the transducer are integrated, either for fixed periods of time or for periods which are necessary to produce a signal of given intensity, and the thus obtained signals are used to regulate the density of the filler by controlling one or more trimming devices and-/or to segregate cigarettes having fillers of unsatisfactory density. The periods of integration of signals from the transducer are shorter than the length of intervals which are necessary to move past the radiation source a portion of the filler whose length equals that of the filler in a cigarette. This renders it possible to regulate the density of tobacco in selected portions, for example at the ends, of discrete cigarettes.

10 Claims, 3 Drawing Figures

METHOD AND APPARATUS FOR MEASURING AND REGULATING THE DENSITY OF ROD-LIKE FILLERS CONSISTING OF TOBACCO OR THE LIKE

This is a continuation of application Ser. No. 480,871, filed June 19, 1974, now abandoned.

BACKGROUND OF THE INVENTION

The present invention relates to a method and apparatus for determining and regulating the characteristics (especially the density) of continuous rod-like fillers consisting of tobacco filaments of a tobacco smoke filtering material or other fibrous substances. More particularly, the invention relates to improvements in a method and apparatus for monitoring the characteristics of a continuous rod-like filler of fibrous material with the aid of a detector including a source of beta rays.

It is known to employ beta ray detectors as a means for determining the density of a continuous rod-like filler consisting of tobacco or filter material. A beta ray detector comprises a radiation source which is located at one side of the path for a continuously moving (wrapped or unwrapped) filler and an ionization chamber or another suitable transducer which is located at the other side of the path opposite the radiation source. The rays which reach the transducer are weakened during passage through the filler so that their intensity indicates the density of the filler and the transducer furnishes a continuous signal whose intensity fluctuates as a function of variations in the density of the filler. Such detectors are often employed in cigarette rod making and analogous machines wherein a continuous rod including a rod-like tobacco filler or a filler consisting of fibrous filter material and a tubular wrapper of cigarette paper or the like is moved lengthwise past a cutoff which subdivides the rod into plain cigarettes, cigarillos, cigars or filter rod sections of unit length or multiple unit length.

It is also known to compensate for those fluctuations in the intensity of beta rays which are attributable to stochastic (randomly occurring) disintegration of nuclei of radioactive material. Such fluctuations are filtered out by resorting to low-pass filters (e.g., R C stages) in order to insure that signals which are used to regulate the operation of the rod-making machine indicate only the density of measured portions of the rod and are not distorted by other phenomena, such as disintegration of nuclei in the source of radioactive radiation. A drawback of presently employed low-pass filters is that their inertia (time constant) is relatively high so that the interval of time which elapses between a measurement and the generation of a signal which indicates the average density of the measured portion of the rod is rather long. Attempts to reduce the length of such intervals include the utilization of high-intensity beta radiation sources (usually strontium 90). This, however, can present a serious danger to the attendants and neccessitates stringent and expensive safety measures. Therefore, manufacturers of smoker's products do not favor the utilization of such density monitoring devices.

If the intensity of beta radiation is reduced to a relatively low value, the delay in generating signals which represent the average density of a rod-like filler of tobacco or filter material is so great that the apparatus employing such monitoring devices cannot be used to determine the average density of relatively short sections of fillers, e.g., sections whose length at most equals that of a plain cigarette or filter plug of unit length. On the other hand, it is often desirable to regulate the density of fillers in cigarettes or other rod-shaped smoker's products in such a way that the density of each and every cigarette or the density of selected portions of discrete cigarettes (e.g.,. of cigarette ends) matches a predetermined value. A prerequisite for such accurate regulation of density is a reliable measurement and immediate indication of density in extremely short portions of a continuously moving rod-like filler.

SUMMARY OF THE INVENTION

An object of the invention is to provide a method which can be utilized for rapid determination of the density of short sections of a continuously moving rod-like filler of fibrous material.

Another object of the invention is to provide a method according to which the measurement of density is affected by resorting to a weak source of corpuscular radiation.

A further object of the invention is to provide a method according to which stochastic fluctuations in the intensity of radiation due to randomly occurring disintegration of nuclei of radioactive material cannot influence the accuracy of measurement and which can be utilized to detect the average density of filler sections having a length which is a small fraction of the length of a cigarette, cigar, cigarillo or filter plug.

An additional object of the invention is to provide an apparatus for the practice of the above outlined method.

The method of the present invention is utilized for measuring the density of a rod-like filler consisting of tobacco, tobacco smoke filtering fibrous material or the like. The method comprises the steps of conveying a filler lengthwise along a predetermined path, positioning a source of beta rays adjacent to one side of the path so that beta rays continuously issuing from the source pass through successive minute increments of the moving filler and their intensity decreases as a function of density of the corresponding increments of the filler, the intensity of beta rays further fluctuating as a result of stochastic disintegration of nuclei of the radiation source, monitoring the intensity of beta rays at the other side of the path opposite the source, producing a continuous succession of first electric signals each of which is indicative of the monitored intensity of beta rays having passed through the respective increments of the filler, and producing a series of second electric signals including continuously integrating the succession of first signals for limited periods of time whereby each second signal represents the average density of that portion of the filler which has been conveyed past the source of beta rays during the corresponding limited period of time.

In accordance with one embodiment of the method, the duration of each limited period may equal a predetermined length of time, i.e., all periods may be of the same duration, and the method may further comprise the step of storing each second signal at least during the generation of the next-following second signal.

In accordance with another embodiment, the method further comprises the steps of comparing the second signals with a reference signal and terminating the integrating step when a second signal matches the reference signal so that the length of the limited periods is a function of the intensity of first signals which together form a second signal. This embodiment of the method also comprises the step of storing each second signal, at least during the generation of the next-following second signal.

In accordance with another embodiment, the method further comprises the steps of comparing the second signals with a reference signal and terminating the integrating stop when a second signal matches the reference signal so that the length of the limited periods is a function of the intensity of first signals which together form a second signal. This embodiment of the method also comprises the step of storing each second signal, at least during the generation of the next-following second signal.

The method may further comprise the step of subdividing the filler (preferably after the filler has been wrapped in a web of cigarette paper or the like) into sections of predetermined length. Each period of time is preferably shorter than the interval which elapses while a filler portion of such predetermined length is being conveyed past the source, and the duration of each interval is preferably a multiple of one of the limited periods.

The method may further comprise the step of producing third signals each having an intensity corresponding to the average intensity of a plurality of successive second signals, and changing the density of the filler upstream of the source as a function of deviation of the intensity of third signals from a predetermined intensity.

The method may further comprise the steps of subdividing the filler into elongated sections downstream of the radiation source whereby the length of each such section exceeds the length of the aforementioned portions of the filler so that at least one second signal is generated during conveying of a section past the source, comparing the intensities of second signals with the intensity of a reference signal, and segregating from the path those sections of the filler whose monitoring resulted in the generation of second signals having an intensity which deviates to a predetermined extent from the intensity of the reference signal. Thus, the method can be used to segregate from satisfactory filler sections all such sections which are too dense or contain insufficient quantities of fibrous material, either along their full length or in selected parts thereof.

The novel features which are considered as characteristic of the invention are set forth in particular in the appended claims. The improved apparatus itself, however, both as to its construction and its mode of operation, together with additional features and advantages thereof, will be best understood upon perusal of the following detailed description of certain specific embodiments with reference to the accompanying drawing.

DESCRIPTION OF THE PREFERRED EMBODIMENTS

Figure 1:
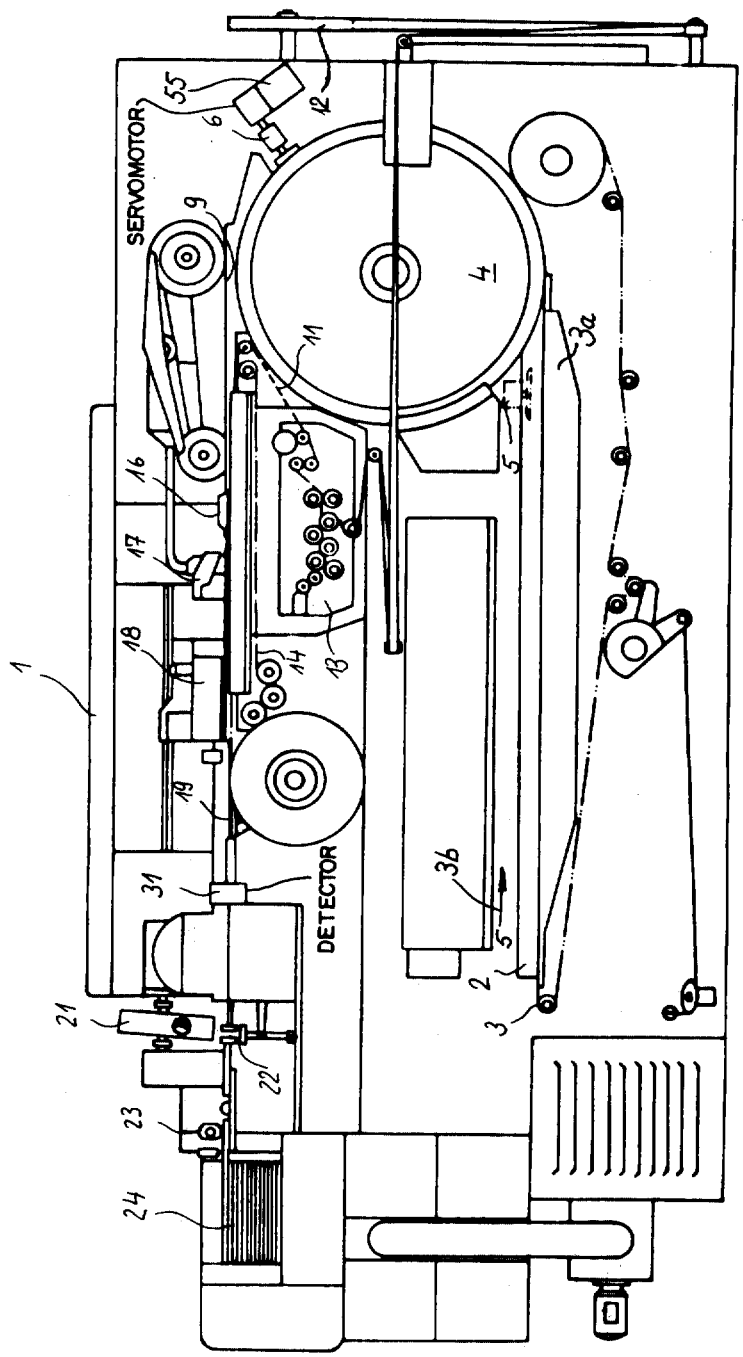
FIG. 1 is a schematic elevational view of a cigarette rod making machine including an apparatus which embodies one form of the invention.

FIG. 1 shows a cigarette rod making machine of the type known as GARANT (trademark) produced by Hauni-Werke, Hamburg-Bergedorf, Western Germany. The machine comprises a distributor 1 which forms a homogeneous layer of tobacco shreds and showers the leading edge of the layer into an elongated channel 2 wherein the shreads descend onto and travel with the upper stretch of an endless tobacco belt 3 to form thereon a growing tobacco stream. The belt 3 is foraminous and its upper stretch travels above the open upper side of a stationary suction chamber 3a which insures that all shreds share the lengthwise movement of the upper stretch of the belt 3 (see the arrow 3b). The fully grown tobacco stream on the right-hand portion of the belt 2 is trimmed by a first adjustable equalizing device 5 which is installed immediately ahead of or close to the locus where the tobacco stream enters the peripheral groove of a suction wheel 4. The latter is driven to rotate anticlockwise, as viewed in FIG. 1, and the bottom wall of its groove has perforations and travels about a stationary suction chamber (not shown) which attracts the tobacco stream to the wheel 4 during transport past a second adjustable trimming or equalizing device 6 which completes the conversion of the stream into a rod-like tobacco filler.

A suction conveyor 9 transfers successive increments of the filler from the groove of the suction wheel 4 onto the upper stretch of a belt conveyor 14, known as garniture, which advances the filler through a wrapping mechanism wherein the filler is confined in a tubular wrapper consisting of a web 11 of cigarette paper or the like. The web 11 is being withdrawn from a roll 12 and passes through an imprinting mechanism 13 before it reaches the upper stretch of the garniture 14. The mechanism 13 applies to longitudinally spaced portions of the web 11 printed matter which may constitute the name of the manufacturer, the brand name of the cigarettes and/or other information. The garniture 14 entrains the web 11 through the wrapping mechanism which includes means 16 for draping the web around the rod-like filler so that one marginal portion of the draped web extends tangentially of the filler and can be coated with a film of adhesive by a paster 17. The thus coated marginal portion of the draped web 11 is thereupon folded over the other marginal portion to form therewith a longitudinally extending seam which is heated by a sealer 18 to complete the conversion of tobacco shreds and web 11 into a continuous cigarette rod 19. The rod 19 passes through a density monitoring device or detector 31 and thereupon enters a cutoff 21 which severs the rod at regular intervals to form a single file of plain cigarettes of unit length or multiple unit length. The orbiting blade or blades of the cutoff 21 sever that portion of the rod 19 which passes through a tubular guide 22. Successive plain cigarettes are thereupon accelerated by a rotary cam 23 which propels them into successive axially parallel flutes of a drum-shaped transfer conveyor 24. The latter serves to convert the single file of plain cigarettes into one or more rows wherein the cigarettes move sideways. Such rows are introduced into a filter cigarette making machine, a packing machine, a tray filling apparatus, or directly into storage.

Figure 2:
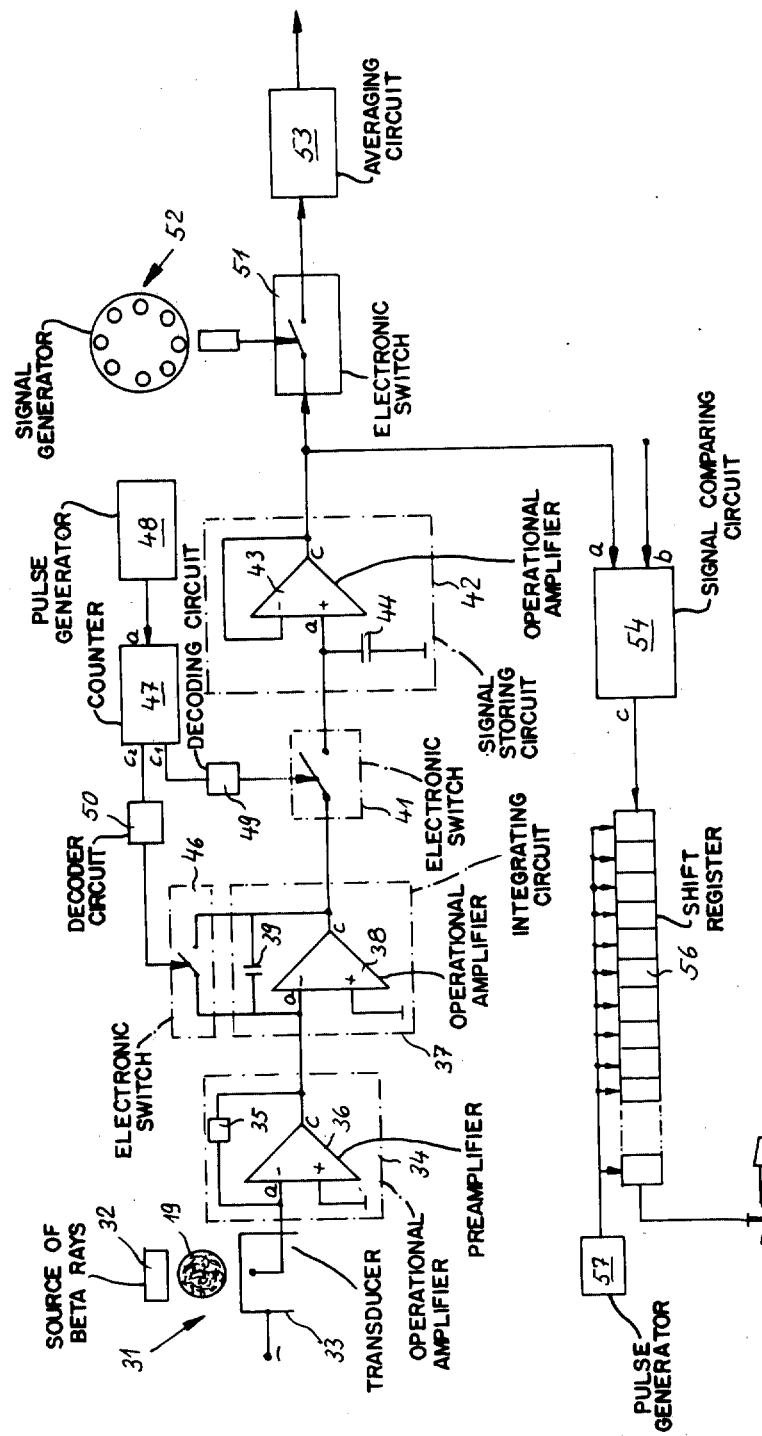
FIG. 2 is a circuit diagram of the apparatus.

The monitoring device 31 forms part of a density measuring and regulating apparatus which is shown in FIG. 2 and includes means for producing signals indicating the average density of selected portions of or the entire filler in the cigarette rod 19. The device 31 comprises a source 32 of beta rays (e.g. strontium 90) which is mounted at one side of the path for the rod 19 and a transducer 33 which is mounted at the other side of the path opposite the source 32. The transducer 33 may constitute an ionization chamber having an output which transmits electric signals to the input $a$ of a preamplifier 36 forming part of an operational amplifier 34. Beta rays issuing from the source 32 are weakened during passage through successive minute increments of the filler into the rod 19 so that their intensity (and hence the intensity of (first) signals furnished by the transducer 33) fluctuates in dependency on changes in density of the filler.

The operational amplifier 36 is of the type 1029 produced by Teledyne Philbrick and further comprises a resistor 35 which is connected between the input $a$ and output $c$ of the preamplifier 36. The amplifier 36 has a high input resistance, a high amplification ratio and a low output resistance. The output $c$ of the preamplifier 36 is connected with the input $a$ of a second operational amplifier 38 forming part of an integrating circuit 37 of the type 8007 produced by Intersil. An integrating capacitor 39 of the circuit 37 is connected between the input $a$ and output $c$ of the amplifier 38, and the output $c$ of the amplifier 38 is connected with the input of an electronic switch 41, e.g., a switch of the type 1 H 5001 produced by Intersil.

The output of the switch 41 is connected with the input $a$ of an operational amplifier 43 in a signal storing circuit 42 which further comprises a capacitor 44. One plate of the capacitor 44 is grounded and the other plate is connected to the input $a$ of the amplifier 43. The latter may be of the type LM 741 produced by National Semiconductor.

The capacitor 39 of the integrating circuit 37 can be short-circuited by a second electronic switch 46 which is connected with the output $C_2$ of a counter 47 through the medium of a decoding circuit 50. The switch 46 may be of the type 1 H 5001 produced by Intersil. The switch 41 is connected with the output $c_1$ of the counter 47 by a decoding circuit 49. The input $a$ of the counter 47 is connected to the output of a highly accurate pulse generator 48, e.g., a quartz oscillator circuit which supplies a succession of high-frequency pulses. The counter 47 is of known design; it can be adjusted in such a way that it resets itself to zero after it receives a predetermined number of pulses (e.g., 1000). After each resetting, the counter 47 begins to count anew in response to reception of high-frequency pulses from the generator 48.

The decoding circuit 49 transmits a signal to close the electronic switch 41 shortly before the circuit 50 closes the switch 46. For example, and assuming that the counter 47 is reset to zero after every 1000 pulses, the circuit 49 can close the switch 41 for a short interval of time when the counter 47 receives 997 pulses, and the circuit 50 can close the switch 46 for a short interval of time when the counter 47 receives 999 pulses.

The output $c$ of the amplifier 43 in the signal storing circuit 42 is connected with an averaging circuit 53 by way of an electronic switch 51 which is actuated at intervals by a signal generator 52 operating in synchronism with the cigarette rod making machine of FIG. 1. Thus, the rate at which the switch 51 receives closing signals from 52 is proportional to the speed of lengthwise movement of the cigarette rod 19. Each closing of the switch 51 results in the transmission (to 53) of a signal at a time when the monitoring device 31 scans a selected portion of the filler in the rod 19, i.e., a portion whose density is of interest for eventual adjustment of the means (e.g., 5 and/or 6) which can regulate the density of the filler.

The output of the averaging circuit 53 can be connected with the equalizing device 5 and/or 6 by one or two adjustable servomotors (only the motor 55 for the equalizing device 6 is shown in FIG. 1). Adjustments of the servomotor 55 in response to signals from the averaging circuit 53 cause the knife or knives of the equalizing device 6 to move nearer to or further away from the foraminous bottom wall in the groove of the suction wheel 4 whereby the device 6 respectively reduces or increases the quantity of tobacco per unit length of the filler.

The operation of the apparatus of FIG. 2 is as follows:

Beta rays issuing from the source 32 penetrate through the advancing cigarette rod 19 and are weakened to the extent which is determined by the density of those minute increments of the filler which pass between the source 32 and transducer 33. The transducer 33 transmits a continuous series of first electric signals to the input $a$ of the preamplifier 36 in the operational amplifier 34. The intensities of first signals furnished by the transducer 33 fluctuate not only as a result of variations in density of the respective minute increments of the filler in the rod 19 but may also fluctuate to a considerable extent as a result of stochastic fluctuations, i.e., as a result of accidentally arising disintegration of nuclei of the radioactive preparation constituting the source 32. This is particularly felt when the source 32 is relatively weak (e.g., in the range of 5 millicurie).

Successive first signals from transducer 33 (inclusive of stochastic fluctuations) are amplified by the operational amplifier 34 and are transmitted to the input $a$ of the amplifier 38 in the integrating circuit 37. The latter integrates (totals) such first signals for successive predetermined equal periods of time. A second signal which is indicative of the sum of first signals supplied by the amplifier 34 appears as a voltage signal at the capacitor 39. The limited equal periods of intergration are determined by the counter 47 and by the setting of decoding circuit 50 which can close the electronic switch 46. As stated above, the pulse generator 48 transmits to the counter 47 pulses at identical intervals and for identical periods of time.

The decoding circuit 49 closes the electronic switch 41 when the counter 47 accumulates a predetermined number of pulses (e.g., 997) which is slightly less than the maximum number of pulses (e.g., 1000) capable of being accepted by counter 47 prior to resetting to zero. The switch 41 closes for a short interval of time and transmits a second signal from the capacitor 39 to the signal storing circuit 42. Such signal is stored in 42 at least during that interval which is needed for generation of the next-following second signal.

Shortly thereafter (i.e., so soon thereafter as is still sufficient for transmission of a signal prior to resetting of the counter 47), the decoding circuit 50 closes the electronic switch 46 (e.g., when the counter 47 accumulates 999 pulses) for a short interval of time so that the capacitor 39 discharges before the counter 47 begins to count a fresh series of pulses supplied by the pulse generator 48. The just described procedure is repeated again and again, always shortly before the counter 47 is reset to zero. The signal storing circuit 42 receives a succession of second signals in response to repeated closing of the electronic switch 41 whereby each second signal represents the sum of first signals which have been supplied to the integrating circuit 37 during the preceding period of accumulation of 997 pulses by the counter 47. Each second signal which is transmitted to the signal storing circuit 42 is indicative of the average density of the filler in that portion of the rod 19 which has passed through the gap between the parts 32, 33 of the monitoring device 31 during the period which elapsed while the counter 47 was in the process of accumulating 997 pulses. The intervals at which the circuit 42 receives second signals from the integrating circuit 37 are constant, and such signals are stored in the circuit 42 in the form of analog voltage signals until after the next-following closing of the electronic switch 51.

The duration of periods of integration of first signals furnished by the transducer 33 can be extremely short in spite of the weakness of radiation supplied by the source 32. Integrated signals which are furnished by the circuit 37 in response to closing of the switch 41 may be indicative of the density of extremely short portions of the cigarette rod 19, for example, of the length of small fractions of discrete plain cigarettes which are formed by the cutoff 21 of FIG. 1. Thus, the signal storing circuit 42 can receive integrated signals each of which is indicative of the average density of the filler in the one or the other end portion or in a median portion of a plain cigarette. When the switch 51 is closed by the signal generator 52, the signal from output $c$ of the amplifier 43 is transmitted to the input of the averaging circuit 53. The latter transmits to the servomotor 55 a signal which is indicative of the average intensity of several second signals supplied by the integrating circuit 42, i.e., the output of the circuit 53 transmits averaged (third) signals of previously averaged (second) signals. As stated above, the signals which are being supplied by the circuit 42 may represent the densities of selected short (end and/or median) portions of the filler such as correspond to small fractions of fillers in discrete plain cigarettes. The timing of transmission of second signals from the integrating circuit 42 to the averaging circuit 53 can take place at intervals which are independent of the speed of the cigarette rod making machine, e.g., at intervals which are necessary to determine the average density of one or more selected portions of successive sections of the rod 19 which sections are to form discrete plain cigarettes downstream of the cutoff 21. Thus, the rate at which the pulse generator 48 transmits signals to the coupler 47 need not be synchronized with the rate at which the cigarette rod making machine produces the rod 19, namely with the rate of transmission of signals from the generator 52 to the electronic switch 51.

It is clear that the length of intervals at which the electronic switch 41 opens to allow for transmission of integrated signals from the circuit 37 to the circuit 42 can be selected in such a way that, at a normal operating speed of the machine, the length of intervals between successive closings of the switch 41 corresponds to the interval which is necessary to advance a full section of the rod 19 past the monitoring device 31, e.g., to move past the transducer 33 that portion of the rod 19 which is to form a discrete plain cigarette of unit length or multiple unit length. The averaging circuit 53 can be used to furnish signals which are indicative of the average density of entire plain cigarettes or of average density of selected portions of plain cigarettes. For example, signals furnished by the circuit 53 can be indicative of the density of the ends of successive plain cigarettes, of the density of median portions of successive plain cigarettes, of the density of median and one or both end portions of successive plain cigarettes, or of the average density of each plain cigarette. This renders it possible to regulate the density of the filler at the first and/or second equalizing station (trimming device 5 and/or 6) in dependency on the desired density of one or more selected portions of plain cigarettes or on the desired average density of entire plain cigarettes.

It is further possible to transmit signals from the output of the signal storing circuit 42 to the input $a$ of a signal comparing circuit 54 whose second input $b$ receives a reference signal from a potentiometer or another suitable rated value selecting means, not shown. If the intensity of signals at the input $a$ deviates to a predetermined extent from the intensity of reference signal at the input $b$ of the circuit 54, the output $c$ of this circuit transmits a signal to the first stage of a shift register 56 or an analogous time-delay circuit which transports the thus received signal at the rate at which the corresponding (defective) plain cigarette approaches an objecting or segregating station including an ejector nozzle 50. When the signal which is supplied by the output $c$ of the circuit 54 reaches the last stage of the shift register 56, such signal opens a normally closed valve 58 which connects the nozzle 59 with a source of pressurized fluid (e.g., compressed air) whereby the fluid expels the defective plain cigarette from the path, e.g., from the corresponding flute of the transfer conveyor 24 shown in FIG. 1. The reference character 57 denotes a pulse generator which transmits to each stage of the shift register 56 pulses at a rate corresponding to the speed of the cigarette rod making machine; this insures that the signal which is supplied by the circuit 54 passes through successive stages of the shift register 56 at the exact speet at which a defective plain cigarette approaches the segregating station. The valve 58 may constitute a solenoid-operated valve which opens for a short interval of time in response to reception of a signal from the last stage of the shift register 56. The signal comparing circuit 54 can be set up in such a way that its output $c$ transmits a signal to the fist stage of the shift register 56 only when the difference between the intensity of a second signal from the signal storing circuit 42 and the intensity of reference signal supplied to the input $b$ of the circuit 54 is sufficient to warrant segregation of the corresponding article because the article is defective owing to excessive or insufficient density of a portion of its filler or unsatisfactory density of the entire filler.

In the apparatus of FIG. 2, changes in the density of filler in the rod 19 cause changes in the amplitude of second signals at the output of the integrating circuit 37. The determination whether the second signals represent the density of a portion of or an entire cigarette is made by the electronic switch 51 and generator 52. When the speed of the rod 19 changes, the length of that portion of the filler in the rod which has caused the generation of a second signal also changes.

Figure 3:
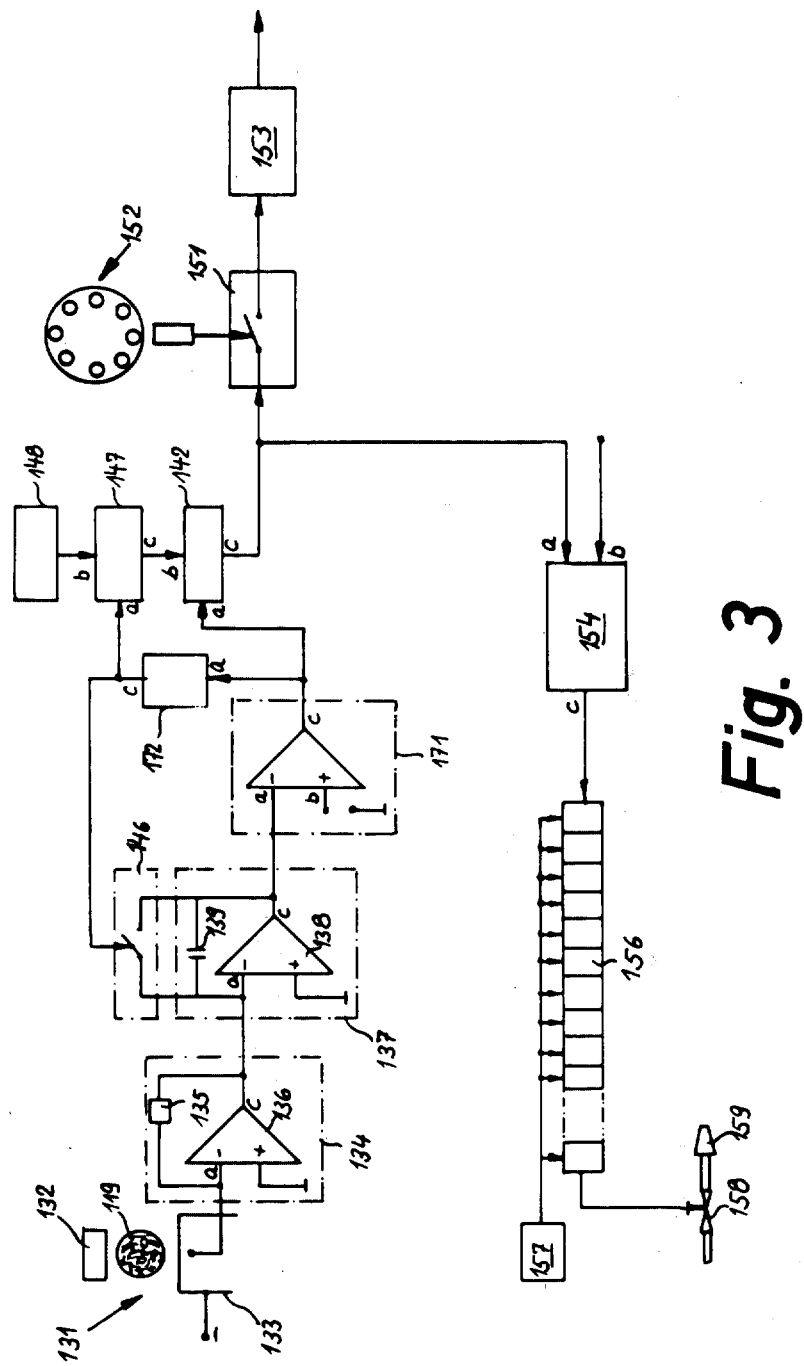
FIG. 3 is a circuit diagram of a modified apparatus.

FIG. 3 shows a modified apparatus which differs from the first apparatus in that a digital signal storing circuit 142 need not receive averaged second signals at regular intervals. The length of such intervals corresponds to the periods of time which the integrating circuit 137 requires to generate second signals of predetermined intensity. All such parts of the apparatus of FIG. 3 which are identical with or clearly analogous to corresponding parts of the first apparatus are denoted by similar preference characters plus 100.

The output $c$ of the amplifier 138 in the integrating circuit 137 is connected with the input $a$ of a signal comparing circuit 171 which may be of the type LM 311 produced by National Semiconductor. The input $b$ of the circuit 171 receives a reference signal of given intensity. The output $c$ of the circuit 171 is connected with the input $a$ of the digital signal storing circuit 142 and also with the input $a$ of a time-delay circuit 172. The output $c$ of the circuit 172 is connected with the electronic switch 146 for the integrating capacitor 139 and with the input $a$ of a digital counter 147. The input $b$ of the counter 147 is connected with a highly accurate pulse generator 148, and the output $c$ of the counter 147 is connected with the input $b$ of the circuit 142.

The operation of the apparatus of FIG. 3:

The (first) signals from transducer 133 (ionization chamber) of the density monitoring device 131 are indicative of the density of successive minute increments of the tobacco filler in the rod 119 and are amplified at 134 prior to being transmitted to the integrating circuit 137. Successive signals from the output $c$ of the pre-amplifier 136 are integrated and the potential difference between the plates of the capacitor 139 is indicative of the intensity of the integrated second signal. Such signal is continuously applied to the input $a$ of the circuit 171 which compares the signal at $a$ with the reference signal at the input $b$. When the intensity of second signal at the output of the integrating circuit 137 matches the intensity of reference signal at the input $b$ of the circuit 171, the output $c$ of the circuit 171 transmits a signal to the input $a$ of the digital signal storing circuit 142; this triggers the transmission of a signal from the output $c$ of the counter 147 to the input $b$ of the circuit 142 whereby the intensity of a further signal at the input $b$ of the circuit 142 corresponds to the number of pulses stored in the counter 147.

The signal from the outlet $c$ of the circuit 171 is further transmitted to the circuit 172 which resets the counter 147 to zero with a minimal delay following the transmission of a signal to the input $b$ of the circuit 142. The signal at the output $c$ of the circuit 172 further closes the electronic switch 146 which discharges the capacitor 139 in the integrating circuit 137. The closing of switch 146 is of very short duration. The circuit 137 is then ready to begin a fresh integrating operation.

The circuit 142 receives from the output $c$ of the counter 147 a signal which is indicative of the duration of the period required by the circuit 137 to furnish to the input $a$ of the circuit 171 a signal whose intensity matches the intensity of reference signal at the input $b$ of the circuit 171. Since the circuit 171 can transmit a signal in digital form, the apparatus of FIG. 3 is particularly suited for highly accurate measurement and evaluation of density by resorting to digital circuits. The evaluation by means of components 151–154 and 156–159 shown in FIG. 3 is analogous to that of similarly referenced parts 51–54 and 56–59 FIGS. 1–2.

In the apparatus of FIG. 3, changes in the density of filler in the rod 119 cause changes in the frequency of matched second signals which are transmitted by the output $c$ of the circuit 142.

An important advantage of the improved method and apparatus is that one can obtain highly accurate indications of the average density of extremely short portions of a rod-like filler of fibrous material even if the intensity of radiation (source 32 or 132) is sufficiently low to insure that the radiation source does not represent a danger to the attendants. Furthermore, the measurement of density is accurate in spite of eventual fluctuations in the intensity of beta rays due to disintegration of nuclei in the source 32 or 132. The signals supplied by the circuit 42 or 142 can be utilized not only to regulate the density of the rod-like filler (via 53 or 153) but also to effect segregation of those sections (plain cigarettes) of the wrapped filler whose monitoring resulted in the generation of signals having an intensity which deviates to a predetermined extent from the intensity of a reference signal (at the input $b$ of the circuit 54 or 154).

Without further analysis, the foregoing will so fully reveal the gist of the present invention that others can by applying current knowledge, readily adapt it for various applications without omitting features which fairly constitute essential characteristics of the generic and specific aspects of my contribution to the art and, therefore, such adaptations should and are intended to be comprehended within the meaning and range of equivalence of the claims.

What is claimed as new and desired to be protected by Letters Patent is set forth in the appended claims.

1. A method of measuring changes in the density of a rod-like filler consisting of tobacco, tobacco smoke filtering fibrous material or the like, comprising the steps of conveying said filler lengthwise along a predetermined path; positioning a source of beta radiation adjacent to one side of said path so that beta rays issuing from said source pass across successive minute increments of the moving filler and their intensity decreases as a function of density of the corresponding increments of said filler, the intensity of said rays fluctuating as a result of stochastic disintegration of nuclei of said source; monitoring the intensity of said rays at the other side of said path opposite said source; producing a continuous succession of first electric signals each of which is indicative of the monitored intensity of rays having passed through an increment of said filler; and generating a series of second signals including continuously integrating said succession of first signals for limited periods of time whereby each second signal represents the average density of that portion of said filler which has been conveyed past said source during the corresponding limited period of time.

2. A method as defined in claim 1, wherein the length of each of said limited periods of time equals a predetermined length.

3. A method as defined in claim 2, further comprising the step of storing each of said second signals, at least during the generation of the next-following second signal.

4. A method as defined in claim 1, further comprising the steps of comparing said second signals with a reference signal and terminating said integrating step when a second signal matches said reference signal so that the length of said limited periods of time is a function of the intensities of first signals which together form said second signals.

5. A method as defined in claim 4, further comprising the step of storing each of said matched second signals, at least during the generation of the next-following second signal.

6. In a machine wherein a rod-like filler consisting of tobacco, tobacco smoke filtering fibrous material or the like is conveyed lengthwise along a predetermined path and is subdivided into sections of predetermined length, apparatus for measuring changes in the density of said filler comprising a monitoring device including a source of beta radiation adjacent to one side of said path and arranged to emit beta rays across successive minute increments of said filler whereby the intensity of rays issuing from said filler decreases as a function of the density of the corresponding increments, the intensity of said rays fluctuating as a result of stochastic disintegration of nuclei of said source, said device further including transducer means adjacent to the other side of said path opposite said source and arranged to produce a continuous succession of first electric signals each of which is indicative of the monitored intensity of rays having passed through an increment of said filler; and means for continously integrating said succession of first signals for limited periods of time to generate second signals each of which represents the average density of that portion of said filler which has been conveyed past said source during the corresponding period of time.

7. Apparatus as defined in claim 6, further comprising means for starting and arresting said integrating means at such intervals that the intensity of each second signal matches a predetermined intensity.

8. Apparatus as defined in claim 7, wherein said integrating means comprises a first electric circuit having an input for first signals connected to said transducer means and an output for second signals, said means for starting and arresting comprising a signal comparing second circuit having a first input connected with said output, a second input receiving a third signal of said predetermined intensity, and an output which furnishes a fourth signal when the intensity of a second signal at said first input matches the intensity of said first third signal, and means for temporarily opening said first circuit in response to said fourth signal.

9. Apparatus as defined in claim 8, wherein said means for temporarily opening said first circuit comprises a switch connected in said first circuit and means for actuating said switch in response to said fourth signals.

10. Apparatus as defined in claim 8, further comprising a signal storing third circuit having a first input connected with the output of said second circuit, a second input and an output, a resettable counter having an output for fifth signals whose intensity increases as a function of time, said last named output being connected with said second input of said third circuit and said third circuit being arranged to transmit fifth signals from said second input to said output thereof in response to transmission of a fourth signal to said first input thereof whereby the intensity of fifth signals at said output of said third circuit is proportional to the duration of said periods.

* * * * *